United States Patent
Lippold et al.

(10) Patent No.: US 6,936,223 B2
(45) Date of Patent: Aug. 30, 2005

(54) CHEMICAL INDICATOR

(75) Inventors: Thomas G. Lippold, Fullerton, CA (US); Nitu Kohli, Lake Forest, CA (US); Pascale D. Endo, Fountain Valley, CA (US); Henry K. Hui, Laguna Niguel, CA (US); Szu-Min Lin, Laguna Hills, CA (US)

(73) Assignee: Ethicon, Inc., Somerville, NJ (US)

( * ) Notice: Subject to any disclaimer, the term of this patent is extended or adjusted under 35 U.S.C. 154(b) by 168 days.

(21) Appl. No.: 10/112,187

(22) Filed: Mar. 28, 2002

(65) Prior Publication Data

US 2002/0151084 A1 Oct. 17, 2002

Related U.S. Application Data

(63) Continuation of application No. 09/312,195, filed on May 14, 1999, now Pat. No. 6,410,338.

(51) Int. Cl.⁷ .............................................. A61L 9/00
(52) U.S. Cl. .............................. 422/58; 422/61; 436/1; 436/164; 436/166; 436/169
(58) Field of Search ............................... 422/56, 58, 61; 436/1, 164, 166, 169

(56) References Cited

U.S. PATENT DOCUMENTS

| | | | |
|---|---|---|---|
| 3,966,414 A | | 6/1976 | Khattab et al. |
| 3,992,158 A | * | 11/1976 | Przybylowicz et al. ........ 422/57 |
| 4,532,107 A | * | 7/1985 | Siddigi ........................ 422/56 |
| 5,278,075 A | * | 1/1994 | Stone .......................... 436/73 |
| 5,518,927 A | | 5/1996 | Malchesky et al. |
| 6,436,716 B1 | * | 8/2002 | Wu ............................. 436/128 |

OTHER PUBLICATIONS

DERWENT–ACC–No: 1996–094441; partial translation of JP 08003494 A published Jan. 9, 1996.*

* cited by examiner

*Primary Examiner*—Lyle A. Alexander
(74) *Attorney, Agent, or Firm*—Blakely, Sokoloff, Taylor & Zafman, LLP

(57) ABSTRACT

A chemical indicator of an aurin moiety in a substrate to detect the presence of an oxidizing agent.

4 Claims, 4 Drawing Sheets

CHEMICAL INDICATOR

This is a continuation of Ser. No. 09/312,195, filed on May 14, 1999, entitled, CHEMICAL INDICATOR now U.S. Pat. No. 6,410,338.

BACKGROUND OF THE INVENTION

1. Field of the Invention

The invention relates to chemical indicators.

2. Description of Related Art

Chemical indicators are used in many processes as a diagnostic tool to indicate whether a desired process or reaction has taken place. One important use of chemical indicators is in the medical industry in sterilization systems to visually indicate whether a sterilization process has taken place. For example, many medical instruments must be sterilized prior to use on a patient. Thus, instrument manufacturers often sterilize instruments before providing them to hospitals, and hospitals generally have their own sterilization systems to sterilize instruments prior to use on a patient. One popular type of sterilizer is the STERRAD® brand of sterilizers manufactured by Advanced Sterilization Products, of Irvine, Calif., a division of Ethicon, Inc. of Somerville, N.J.

The STERRAD® sterilizers are designed to house one or more removable trays that fit within a sterilization chamber. Each tray may be filled with medical instruments such as scalpels, endoscopes, scissors, and the like. To sterilize the medical instruments, the sealed chamber is exposed to a vacuum and hydrogen peroxide or other oxidizing agent vapor is introduced into the chamber. Hydrogen peroxide is a popular oxidizing agent because of its potent sporicidal effect as well as its ability to decompose readily into water and oxygen after the sterilization process making the sterilization chamber safe for human contact.

As a way to demonstrate that a sterilant such as hydrogen peroxide is present in a sterilization chamber of a sterilizer (e.g., a STERRAD® sterilizer), a chemical indicator that is sensitive to the sterilant is placed in the chamber along with the items to be sterilized. A popular form of chemical indicator is a strip of paper or other substrate with a dye adhered to one side of the substrate. A visible change in the dye of the chemical indicator, such as a color change, indicates that the items contained within the chamber have been exposed to the sterilant.

Previous chemical indicators for sterilization processes such as described rely upon dyes that are sensitive to changes in pH. Exposure to an oxidizing sterilant (e.g., hydrogen peroxide) generally changes the pH in the sterilization chamber from basic to acidic. The dye of the prior art chemical indicators are generally acid-base indicators and change color as the pH of the system changes.

One problem with prior art chemical indicators used in the manner described is that the dye is generally not permanently changed after the sterilization process and thus the color change may be reversed under certain conditions such as exposure to a basic environment. For example, a popular pH-sensitive dye is a phenol red dye adhered to a paper substrate. The phenol red dye changes from a red to yellow color when the chemical indicator is exposed to an acidic environment such as a hydrogen peroxide sterilant. It has been found, however, that the color change could be reversed under exposure to a basic environment.

A further problem with prior art chemical indicators such as the phenol red chemical indicator, is that the indicator is generally not specific, for example, to the oxidant for which it is to be used. Instead, the phenol red chemical indicator will change color in response to a change in pH brought about by any agent, including environmental factors. Some factors that may cause a premature or undesired color change include ambient light, instability of the chemical formulation, and environmental contaminants. Thus, the phenol red chemical indicator is often combined with other agents, such as ultraviolet light stabilizers or hydrophilic agents to resist undesired changes in color. The non-specificity of the phenol red chemical indicator yields stability problems both in the storage of the chemical indicator as well as evidencing a prior test result.

What is needed is a chemical indicator, particularly for oxidation-type sterilization processes that offers a non-reversible color change and is chemically stable.

SUMMARY OF THE INVENTION

A chemical indicator is disclosed. In one aspect of the invention, the chemical indicator comprises an aurin moiety in a substrate to detect the presence of an oxidizing agent. In one embodiment, the aurin moiety is one of the ammonium salt and the sodium salt of aurintricarboxylic acid.

A method is also disclosed including, in one embodiment,

Exposing an indicator comprising an aurin moiety to an oxidizing agent, and detecting the exposure by a color change of the aurin moiety.

A system is further disclosed. In one embodiment, the system includes an apparatus comprising a chamber adapted to retain one or more of articles and a receiver coupled to the chamber in a manner to introduce an oxidizing agent from the receiver into the chamber. The system further includes an indicator comprising an aurin moiety exposed to the chamber and comprising a portion that changes color upon exposure to an oxidizing agent.

Additional features, embodiments, and benefits will be evident in view of the figure and detailed description presented below.

BRIEF DESCRIPTION OF THE DRAWINGS

The features, aspects, and advantages of the invention will become more thoroughly apparent from the following detailed description, appended claims, and accompanying drawings in which:

DETAILED DESCRIPTION OF THE INVENTION

The invention relates to a chemical indicator particularly useful for oxidation-type sterilization processes. In one aspect of the invention, the chemical indicator comprises an aurin moiety in a substrate to detect the presence of an oxidizing agent. In one embodiment, the aurin moiety comprises a salt of aurintricarboxylic acid such as the ammonium or sodium salts of aurintricarboxylic acid.

One use for the chemical indicator of the invention is to detect the presence of an oxidative germicide. In the presence of an oxidizing agent, the chemical indicator changes color. For example, the triammonium or trisodium salt of aurintricarboxylic acid changes from a red color to a tan/gold color in the presence of an oxidizing agent. Thus, the chemical indicator may be used as a diagnostic tool to detect the presence of an oxidizing agent in a system such as a sterilization system.

One benefit of the chemical indicator of the invention is that the color change is generally irreversible. After a color change brought about by an oxidizing agent, exposure of the chemical indicator to other agents, such as reducing agents or acids or bases generally will not cause a color change. This is believed to be the result of a transformation of the molecular structure of the aurin moiety upon exposure to the oxidizing agent.

The chemical indicator of the invention may be embodied in several forms, examples of which will be described below. In this manner, the chemical indicator may be used in a variety of systems. For example, the chemical indicator may be used to detect the presence of an oxidizing agent that is in, for example, a gas or liquid phase.

Figure 1:
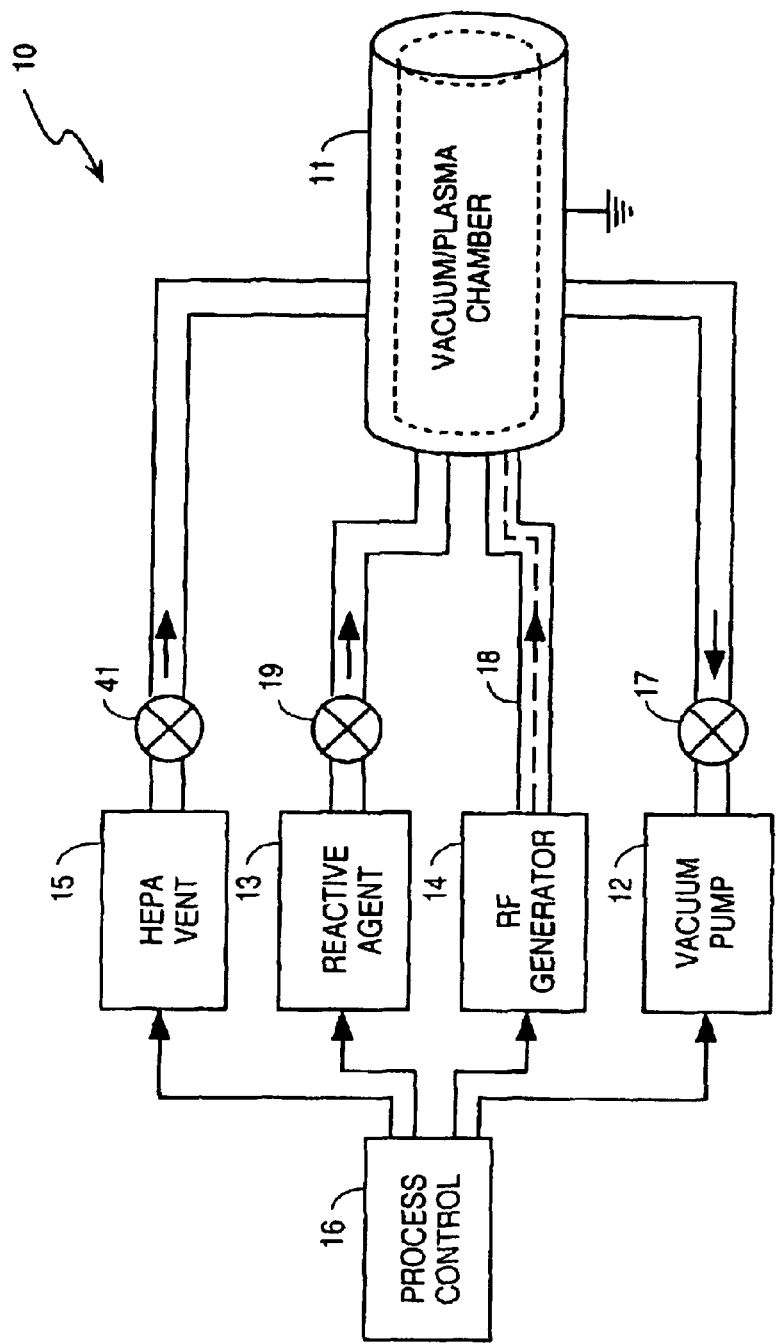
FIG. 1 illustrates a diagram of an embodiment of a plasma sterilizer system.

One use for the chemical indicator of the invention is to indicate the presence of a sterilizing agent in a sterilization chamber such as, for example, a STERRAD® hydrogen peroxide gas plasma type sterilizer in a STERRAD® sterilization process developed by the assignee. One STERRAD® process is performed in the following manner schematically illustrated by system 10 in FIG. 1. The article(s) to be sterilized is(are) placed in sterilization chamber 11, the chamber is closed, and a vacuum is drawn, for example, by vacuum pump 12. An aqueous solution of reactive agent 13 of, for example, a sterilizing agent such as hydrogen peroxide, is injected and vaporized into the chamber so that it diffuses onto the article(s) to be sterilized and the pressure in sterilization chamber 11 is reduced. The hydrogen peroxide is left in contact with the article(s) for a period of time to kill microorganisms thereon. A low-temperature gas plasma is then initiated by applying radio frequency (RF) energy from RF generator 14 to create an electrical field. In the plasma, the hydrogen peroxide is disassociated into reactive species that collide/react with and kill microorganisms. The term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, an RF or microwave is commonly used. The plasma is maintained for a sufficient time to achieve sterilization and convert residual hydrogen peroxide into water and oxygen. After completion of the process, the RF energy is turned off, the vacuum is released, for example, through vent 15, and the chamber is returned to atmospheric pressure by the introduction of filtered air. In FIG. 1, process control logic 16 is connected to each of the components of sterilization system 10 that are connected to sterilization chamber 11. In general, gas plasma can be used to remove residual sterilant and to enhance the sterilization efficacy as described in U.S. Pat. Nos. 4,643,867 and 4,756,882 which are incorporated herein by reference. The chemical indicator of the invention may also be used in systems described in U.S. Pat. Nos. 5,656,238; 5,115,166; and 5,087,418, which are also incorporated herein by reference, in which the article(s) to be sterilized is(are) located in a chamber that is separated from the plasma source.

It is to be appreciated that the chemical indicator of the invention is not limited to uses associated with the STERRAD® sterilization process. Instead, the chemical indicator of the invention may find use in a myriad of applications including plasma sterilization processes. The STERRAD® sterilization process should be viewed as exemplary of such myriad of applications.

In the embodiment described above, the sterilant or sterilizing agent is, for example, hydrogen peroxide. Hydrogen peroxide is a known oxidizing agent. To verify that the sterilizing agent (oxidizing agent) is supplied to sterilization chamber 11 in sufficient quantity and duration to achieve sterilization of the article or articles within sterilization chamber 11, a chemical indicator in various forms may be used.

The chemical indicator of the invention comprises an aurin moiety in a substrate. General Formula I represents an embodiment of an aurin moiety suitable in the chemical indicator of the invention.

General Formula I

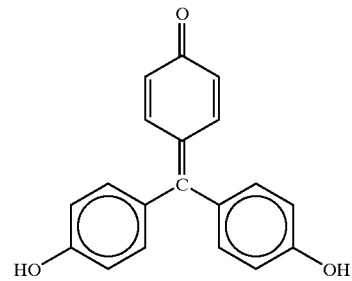

As noted, in one embodiment, the aurin moiety comprises a salt of aurintricarboxylic acid such as the triammonium or trisodium salt of aurin

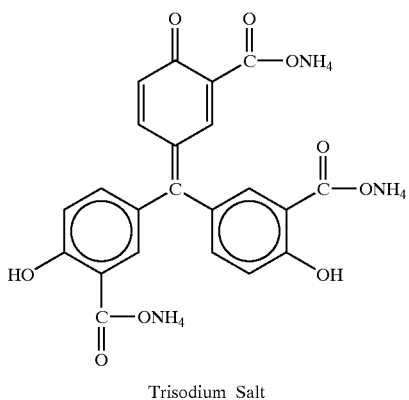

Trisodium Salt tricarboxylic acid as represented below:

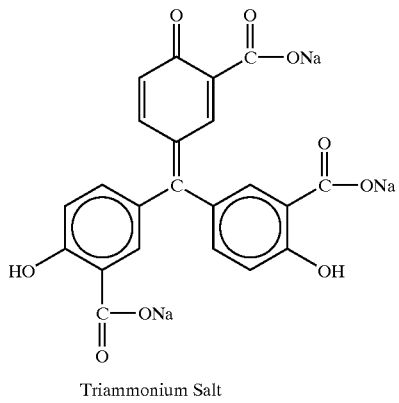

Triammonium Salt

It is to be appreciated that other aurin moiety analogs or salts having similar properties of oxidation sensitivity and non-reversibility are also suitable and contemplated by the invention. For example, sulfate or phosphate acids and salts having an aurin moiety core are believed to be suitable. In one embodiment, the aurin moiety is also water soluble. Water soluble components may be preferable in manufacturing industries, such as the printing industry.

In one embodiment of the chemical indicator of the invention the aurin moiety is adhered to the substrate, such as in a strip or dot (e.g., circular) form. In this form, the chemical indicator may be placed in an environment to monitor the presence of an oxidizing agent. For example, a strip or dot of paper (cellulose), polystyrene, polyester, nylon, polypropylene, or polyethylene having an aurin moiety adhered or coated on a portion of one side of the strip or dot may be placed in sterilization chamber 11 to monitor and evaluate the presence of a sterilizing agent (an oxidizing agent) such as hydrogen peroxide to sterilize medical instruments. The aurin moiety may be adhered to the substrate as one stripe or dot or as a series of stripes or dots. A strip, for example, may have a width of approximately 0.25 inches and a length of two inches. A dot may be circular with a radius of, for example, 0.25 to one inches. It is to be appreciated that various other sizes and shapes of the substrate, e.g., stripes or dots, may be utilized depending, in part, on the application of the chemical indicator. One benefit of the chemical indicator of the invention is that, after such color change of the aurin moiety, exposure of the chemical indicator to acids or bases or other agents generally will not cause a color change, rendering the chemical indicator non-reversible under normal conditions. Thus, the chemical indicator may be stored as evidence of a reaction process, e.g., evidence in a laboratory or quality control notebook that a system was exposed to a sterilizing agent.

The aurin moiety may also be adhered to a substrate such as a strip or dot having an adhesive on a side opposite the aurin moiety, such that the chemical indicator may be used in the form of, for example, a strip of tape to, for example, secure a barrier wrap. A barrier wrap such as a permeable polypropylene or other material wrap is often used in sterilization systems to wrap, for example, medical devices. The wrap inhibits spores and bacteria from contacting the medical devices, but is permeable to a sterilizing agent such as hydrogen peroxide. By securing the wrap around the medical devices with a chemical indicator in the form of a tape (e.g., a strip of tape containing aurin moiety adhered thereto), the sterilization process may be visualized without unwrapping the load, e.g., by looking at the aurin moiety side (i.e., the non-adhesive side) of the substrate to see if the color of the aurin moiety of the chemical indicator has changed (e.g., changed from a red color to a tan/gold color).

Figure 2:
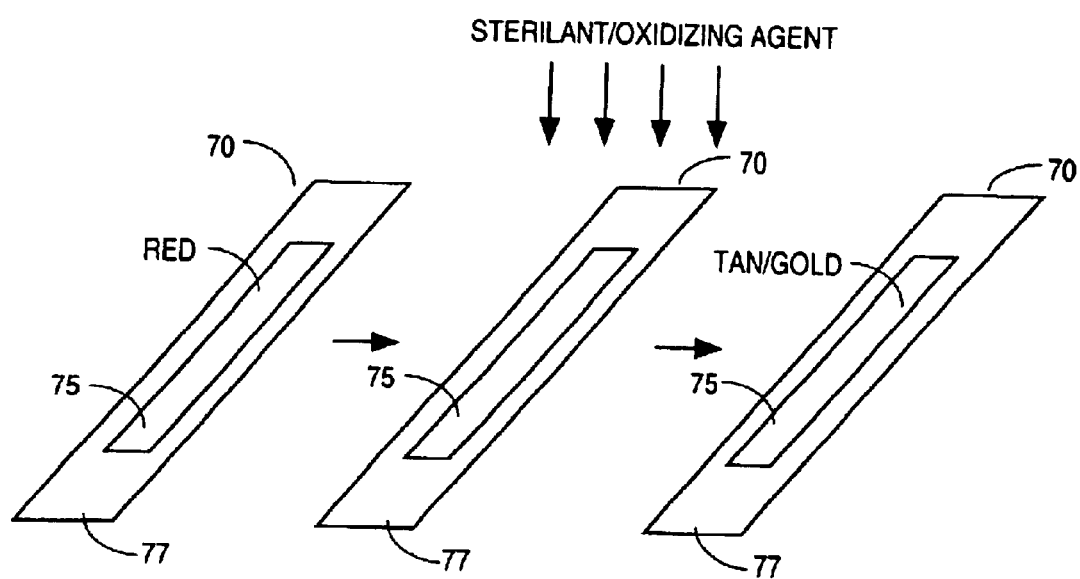
FIG. 2 schematically illustrates a chemical indicator undergoing a color change upon exposure to an oxidizing agent.

FIG. 2 demonstrates a process of exposing the chemical indicator of an embodiment of the invention to a sterilizing agent (an oxidizing agent), such as hydrogen peroxide. In this example, the chemical indicator 70 comprises an aurin moiety 75, such as the ammonium or sodium salt of aurin-tricarboxylic acid adhered to substrate 77, the substrate having representative dimensions of a strip of approximately 0.25 inches by two inches. Prior to exposure, the aurin moiety 75 of chemical indicator 70 is red in color. Upon exposure to an oxidizing agent, such as a sterilizing agent of, for example, hydrogen peroxide, aurin moiety 75 turns to a tan/gold color. Thus, the chemical indicator of the invention changes from a portion with a red color to a portion with a tan/gold color.

In general, the aurin moiety is adhered to the substrate (e.g., strip or dot) through either an aqueous- or organic-based solvent vehicle to form the chemical indicator. Suitable aqueous-based solvent vehicles include deionized water. Suitable organic-based solvent vehicles include low molecular weight alcohols such as propanol or isopropanol. An adherent or binder may further be combined with the aurin moiety in the solvent in forming the chemical indicator. Suitable adherents include, but are not limited to, a nylon-based binder such as VERSAMID™, commercially available from Henkel Corporation of Ambler, Pa., or metallic binder LNG™, commercially available from Vivitone Corporation of Paterson, N.J. The aurin moiety/solvent/binder combination is transferred to a surface of a substrate according to generally known printing techniques.

For compatibility with current generally known printing techniques, a suitable range of aurin moiety:solvent:binder combination is, by weight, 0.1–20%:30–85%:15–75%. It is to be appreciated that the invention is not limited to an article or use of an article or range of a composition of a combination of aurin moiety, solvent, and binder. In fact, it may be that other combinations or ranges may be suitable for a particular adhering process of the fluid to the substrate. Alternatively, in certain instances, the aurin moiety does not need to be combined with a solvent or binder. For instances, in one application, the aurin moiety may be combined with a photosensitive compound and the two-component composition transferred to a substrate using generally known printing techniques. Once transferred, the composition may be exposed to a light source (e.g., ultraviolet light source) to adhere the composition to the substrate via curing of the photosensitive compound.

Typical printing processes for producing a chemical indicator that is a strip or dot include silk screening, gravure, and transfer printing. The silk screening of the aurin moiety generally involves producing a screen by a photographic method in the desired configuration for each aurin moiety to be printed. The screen is exposed under light to a preselected pattern and then developed. The areas of the screen that are not exposed to light, when developed, become porous. However, the areas of the screen that have been exposed to light remain relatively non-porous. The screen is then secured in a frame and the substrate (e.g., strip or dot) placed below. The desired aurin moiety fluid, prepared to have a viscosity sufficient to enable spreading of the fluid, is then spread over the top side of the screen. The aurin moiety passes through the porous areas of the screen and onto the substrate. The substrate is then subjected to a drying process, specific to the aurin moiety.

The gravure method of printing an aurin moiety on a substrate comprises coating a metal surface with a light sensitive polymer. The polymer is exposed to light in the desired predetermined pattern. When developed, the polymer creates hydrophilic and hydrophobic regions. The aurin moiety is prepared such that when applied to the metal it will adhere only to the hydrophilic region. After the prepared aurin moiety is applied, the substrate is pressed against the metal and the aurin moiety is transferred from the metal to the substrate.

The substrate printing method comprises transferring the aurin moiety from a dye to the substrate in the desired pattern. The dye is made with the appropriate pattern on its surface and then coated with the desired, especially prepared aurin moiety. A rubber stamp mechanism is pressed against the dye to transfer the aurin moiety in the desired pattern from the dye to the rubber stamp. The rubber stamp is impressed against the substrate to transfer the aurin moiety, in the same pattern, to the substrate.

Figure 3:
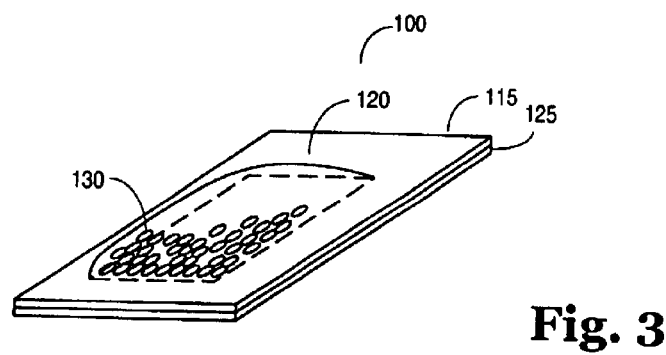
FIG. 3 illustrates an embodiment of the invention of a solid phase aurin moiety in a gas permeable pouch.

In another embodiment, the aurin moiety is a solid, such as the triammonium or trisodium salt of aurintricarboxylic acid in solid form. The solid may be placed, for example, in a substrate that is a reaction vessel to allow an oxidizing agent into the vessel. One substrate illustrated in FIG. 3 is gas permeable pouch 100 such as, for example, a four inch wide by ten inch long pouch of less than one-thousandth of an inch thickness. Solid 130 comprising aurin moiety, possibly mixed with one or more inert constituents, is placed inside pouch 100 and pouch 100 is sealed at its ends. Portion 115 of pouch 100 should have a property such that solid 130 inside the pouch is sufficiently visible to notice the color change. Pouch 100 may be completely gas permeable or may comprise gas permeable portion 115 and gas impermeable portion 125. Spun-bond polyethylene, such as TYVEK® is suitable as gas permeable portion 115 of pouch 100 while a transparent polyester such as MYLAR® is suitable for gas impermeable portion 125 of pouch 100. It is to be appreciated that only a portion of pouch 100 may be transparent, but, to aid the visualization of the oxidation reaction, most of or the entire pouch may be transparent. In one example, pouch 100 is adapted to be placed inside sterilization chamber 11 (see FIG. 1) to detect the presence of a sterilizing agent (e.g., oxidizing agent) through a color change of the aurin moiety in the pouch. Because the oxidation of the aurin moiety is generally irreversible, pouch 100 may be stored after a reaction or test as evidence of a result.

Figure 4:
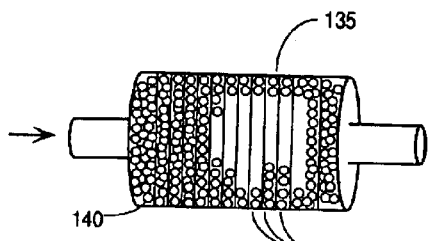
FIG. 4 illustrates an embodiment of the invention of a solid phase aurin moiety in a flow-through reaction vessel.

A second substrate for use with a solid phase aurin moiety in a chemical indicator is illustrated in FIG. 4. FIG. 4 shows a substrate of reaction vessel 135 with, for example, ports or lines to allow the passage of an oxidizing agent, such as a sterilant, through reaction vessel 135. Solid 140 comprising a solid phase aurin moiety 140, possibly with one or more inert constituents, is disposed inside reaction vessel 135. Reaction vessel 135 is coupled, for example, to a port of a reaction chamber, such as vacuum chamber 11 or other reaction chamber. Alternatively, reaction vessel 135 may be located within a reaction chamber such as sterilization chamber 11 (see FIG. 1).

Reaction vessel 135 is preferably transparent so that the color of the solid may be visualized without removing solid 140 from the reaction vessel. Reaction vessel 135 may also contain a series of gradations 138. An oxidizing agent propagated through the reaction vessel along an axis substantially perpendicular to the series of gradations 138 allows a color change of aurin moiety 140 to be observed. The color change may be quantified in terms of a distance to provide an indication about the concentration of the oxidizing agent traveling through reaction vessel 135.

Figure 5:
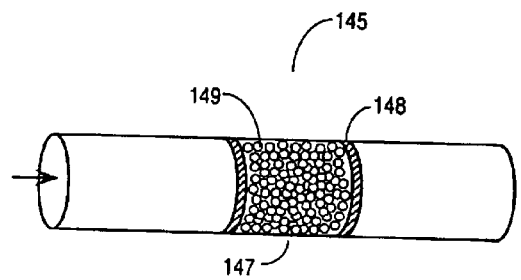
FIG. 5 illustrates an embodiment of the invention of a solid phase aurin moiety in a tube.

A third substrate for use with a solid phase aurin moiety in a chemical indicator is illustrated in FIG. 5. FIG. 5 shows a substrate of tube 145, such as generally hollow tube 145 of, for example, stainless steel, plastic (e.g., polymer) or other material. A portion of tube 145 includes transparent portion 147 such as a transparent polymer. Disposed within transparent portion 147 inside tube 145 is solid 149 comprising a solid phase aurin moiety, possibly with one or more inert constituents. Solid 149 is retained within transparent portion 147 by porous stoppers 148 such as porous glass fiber stoppers disposed on each side of solid 149. In this manner, an oxidizing agent propagated through the opening in tube 145 contacts solid 149 and produces a color change of solid 149 that is visible through transparent portion 147. Tube 145 may be coupled to a reaction chamber, such as a port of sterilization chamber 11 (see FIG. 1) or may be placed inside the reaction chamber.

Figure 6:
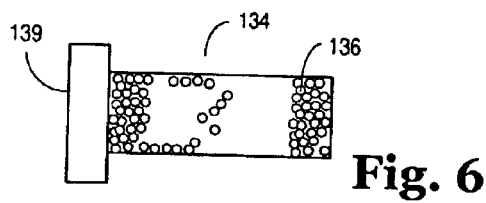
FIG. 6 illustrates an embodiment of the invention of a solid phase aurin moiety in a reaction vessel.

FIG. 6 illustrates a fourth substrate for use with a solid phase aurin moiety in a chemical indicator. FIG. 6 shows a substrate that is a transparent capsule 134 with opening 139 at one end and that is sealed at the other end. In one aspect, to act as a gas process indicator, opening 139 is covered by a gas permeable membrane such as a spun-bound polyethylene (e.g., TYVEK®) Inside capsule 134 is solid 136 comprising solid phase aurin moiety, possibly with one or more inert constituents. In this manner, an oxidizing agent propagated through opening 139 in capsule 134 contacts solid 136 and produces a color change of solid 136 that is visible through capsule 134. Capsule 134 may be coupled to a reaction chamber, such as a port of sterilization chamber 11 (see FIG. 1) or may be placed inside the reaction chamber.

In still another embodiment, the aurin moiety of the chemical indicator of the invention may be in a liquid phase such as a solution form of the triammonium or trisodium salt of aurintricarboxylic acid. The solution may be formed by dissolving an aurin moiety salt in a liquid such as deionized water or a solvent such as a polar solvent, e.g., isopropyl alcohol.

Figure 7:
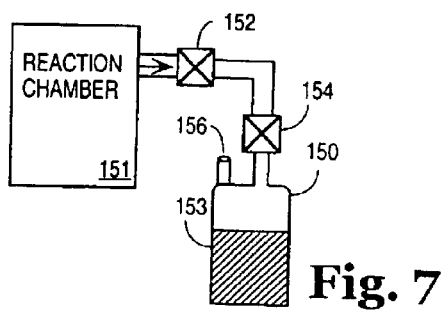
FIG. 7 illustrates an embodiment of the invention of a liquid phase aurin moiety in an ampoule.

FIG. 7 illustrates an example where a substrate of the chemical indicator is ampoule 150 with an inlet port controlled by valves 152 and 154 to allow the passage of an oxidizing agent, such as a sterilizing agent, into ampoule 150 from reaction chamber 151. Ampoule 150 may be coupled, for example, to a port of reaction chamber 151, such as a port of sterilization chamber 11 (see FIG. 1). Thus, ampoule 150 is, in one instance, sealed or sealable and, in another instance, openable. Ampoule 150 may also include purge port 156 to alleviate a pressure build up in ampoule 150. The chemical indicator of this embodiment is suitable for use as a gas or liquid process indicator.

Solution 153 comprising an aurin moiety is disposed inside a portion of ampoule 150. Ampoule 150 is preferably transparent so that the color of solution 153 may be visualized without removing the solution from the reaction chamber. A change in color of solution 153 indicates the presence of an oxidizing agent.

Figure 8:
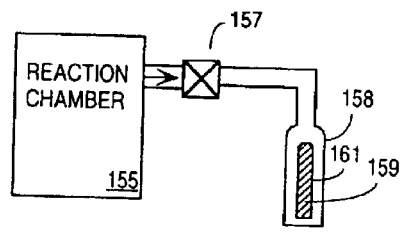
FIG. 8 illustrates an embodiment of the invention of a liquid phase aurin moiety in a compressible ampoule.

FIG. 8 shows a second example of a substrate that is an ampoule for the liquid phase aurin moiety solution. In FIG. 8, ampoule 158 containing solution 159 comprising an aurin moiety contained in sealed inner ampoule 161. Ampoule 158 is coupled, for example, to a port of reaction chamber 155, such as a reaction chamber for a liquid process. Valve 157 regulates the flow of constituents to ampoule 158. To expose contained solution 159 to constituents (e.g., liquid) from reaction chamber 155, valve 157 is opened, to allow the constituents into ampoule 158. Once the constituents are in ampoule 158, valve 157 is closed, and ampoule 158 is compressed to shatter or break inner ampoule 161 containing solution 159. Solution 159 comprising an aurin moiety is then available to interact with, for example, an oxidizing agent of the constituents from reaction chamber 155 and a color change may be visualized.

Figure 9:
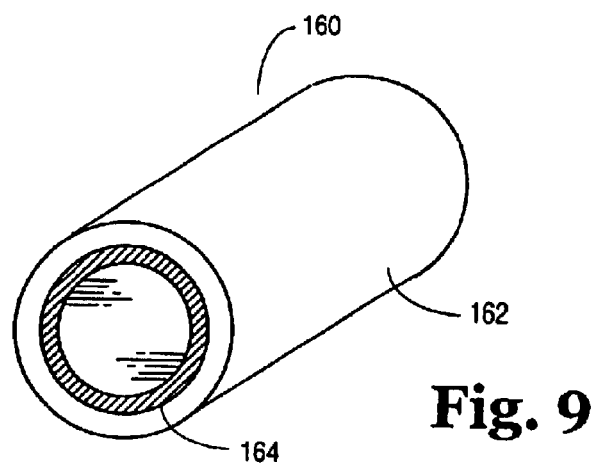
FIG. 9 illustrates an embodiment of the invention of an aurin moiety coated on the inside of a transparent tube.

FIG. 9 illustrates yet another embodiment of the chemical indicator of the invention. In this embodiment, an aurin moiety is coated on a substrate. FIG. 9 shows, for example, chemical indicator 160 including substrate that is, for example, transparent plastic or polymer tube 162 having an opening disposed therethrough. Coated or adhered to the inner wall of tube 162 is aurin moiety 164. Aurin moiety 164 may be coated or adhered to tube 162 by dissolving a salt, such as the triammonium or trisodium salt of aurintricarboxylic acid, in a solvent, such as an evaporable solvent to form a solution; contacting the solution with tube 162; and allowing the solvent to evaporate and the salt to dry on tube 162. In one embodiment, aurin moiety 164 is coated along a sufficient length and area that a change in color of the aurin moiety due to the presence of an oxidizing agent propagated through the opening of tube 162 may be visualized through the exterior surface of tube 162.

Figure 10:
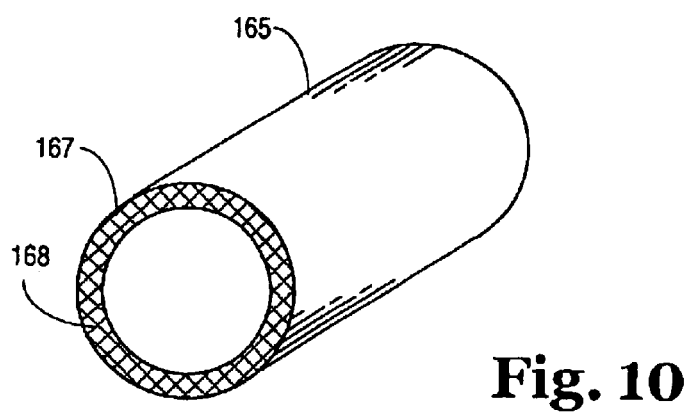
FIG. 10 illustrates an embodiment of the invention of an aurin moiety mixed with a polymer into a tube.
Figure 11:
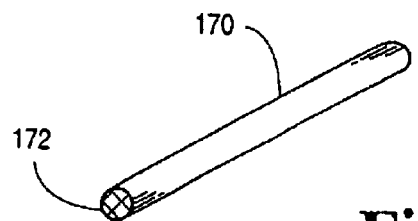
FIG. 11 illustrates an embodiment of the invention of an aurin moiety mixed with a polymer into a solid substrate.

FIG. 10 illustrates a further embodiment of the chemical indicator of the invention, wherein an aurin moiety is mixed with and becomes part of the substrate. In one embodiment, for example, a polymer such as a transparent polyurethane or other transparent polymer or polymers is/are mixed with solid phase aurin moiety particles. One way this is accomplished is by mixing polymer pellets with solid phase aurin moiety particles. The mixture is heated and extruded as known in the art to form chemical indicator 165 of a tubular body including substrate 167 of polymer material and aurin moiety 168 mixed within the substrate matrix. Alternatively, as shown in FIG. 11, the mixture may be extruded into chemical indicator 170 of a solid rod, thread or string of polymer material and aurin moiety 172.

The following examples illustrate the use of the chemical indicator of the invention.

EXAMPLE 1

In one example, a screen printing ink was prepared by mixing 5.0 grams aurintricarboxylic acid, triammonium salt with 12.5 grams deionized water (aqueous solvent), and 32.8 grams metallic binder LNG™. The resulting mixture was screen printed on polystyrene, spun-bound polyethylene, and polyester substrates, respectively. The printed ink was red in color. Upon sterilization in a STERRAD® 100 hydrogen peroxide gas plasma type sterilizer (and exposed to a hydrogen peroxide sterilizing agent), the printed ink of the chemical indicator turned from a red color to a tan/gold color. Processed samples (i.e., samples exposed to a sterilizing agent) show no sensitivity to acids or bases.

The above example demonstrates that the chemical indicator of the invention when exposed to an oxidizing agent will change from a red color to a tan/gold color. The above example also demonstrates that once processed, the change is generally not reversible. In other words, the processed chemical indicator will not change color when exposed to an acidic or basic environment. It has further been demonstrated that the processed chemical indicator is stable under a variety of environmental conditions, including exposure to ultraviolet light or adhesives. Thus, the result of a test or experiment involving the chemical indicator may be stored (in a form of the visual diagnostic indicator) for later reference. Ultraviolet light or other stabilizers need therefore not necessarily be combined with the chemical indicator of the invention, although such stabilizers or other agents may be desired in certain situations.

EXAMPLE 2

In another example, a flexographic ink was prepared by mixing 14.3307 g aurincarboxylic acid, triammonium salt with 66.3399 g Versamid™ 744 (binder) and 120.3491 g 2-propanol (organic solvent) in a blender. The resulting mixture was printed with a flexographic hand proofer on polystyrene, spun-bound polyethylene, and latex-impregnated crepe paper substrates. The printed ink was red in color. The samples were placed in a STERRAD® 100 hydrogen peroxide gas plasma type sterilizer and exposed to 1440 microliters hydrogen peroxide for ten minutes and without plasma at the end of the cycle. The printed ink of the chemical indicator turned from a red color to a tan/gold color, demonstrating that the chemical indicator of the invention will change when exposed to an oxidizing agent and does not require the presence of plasma to effect a color change.

EXAMPLE 3

In a third example, approximately 20 mg each of the following aurin moieties were weighed:

Aurintricarboxylic acid triammonium salt (Aluminon)

Aurintricarboxylic acid trisodium salt

The aurin moieties were placed into separate 4 in.×10 in. TYVEK® pouches. The pouches were heat-sealed and the color of the aurin moieties was recorded using a PANTONE™ color chart. The pouches were placed inside an empty tray and the tray was placed on the top shelf of the STERRAD 100® sterilizer. The load was processed at half cycle using 1140 µl 59% nominal hydrogen peroxide. Upon completion of the cycle, the pouches were removed from the chamber and the color of the post-processed aurin moiety was recorded using the PANTONE™ color chart.

Results:

| Solid Aurin Moiety | Pre-Processed Color | Post-Processed Color | Distinct Color Change |
|---|---|---|---|
| Aurintricarboxylic triammonium salt (Aluminon) | Red 1807C | Brown 1615C | Yes |

-continued

| Solid Aurin Moiety | Pre-Processed Color | Post-Processed Color | Distinct Color Change |
|---|---|---|---|
| Aurintricarboxylic acid trisodium salt | Red 216U | Tan 1395C | Yes |

The two aurintricarboxylic acid salts show distinct color changes from red to brown and tan after they were exposed to hydrogen peroxide vapor with plasma.

EXAMPLE 4

In a fourth example, 0.47 of aurintricarboxylic acid, ammonium salt (Aluminon) was dissolved in 100 ml of deionized water. The solution was thoroughly mixed to ensure that the aurin moiety was totally dissolved. 10 milliliters (ml) of the aurin moiety solution was placed in a test tube. The previous step was repeated until four test tubes were filled. The color of the solution was recorded using a PANTONE™ color chart. The following solutions were added to each of the test tubes:

10 ml of 59% $H_2O_2$ solution (Oxidizer)
4 ml of 5.25% of NaOCl solution (Bleach, oxidizer)
10 ml of 1.0 N NaOH (Base)
8 ml of 1.2 N HCl (Acid)

The reactants were mixed thoroughly and the color of the solutions was recorded over time. The results were tabulated below:

| Vol. of Aurin Moiety | Reactant | Volume of Reactant | Initial Color | Final Color |
|---|---|---|---|---|
| 10 ml | 59% $H_2O_2$ | 10 ml | Red | Yellow |
| 10 ml | Bleach | 4 ml | Red | Light yellow |
| 10 ml | 1.0 N NaOH | 10 ml | Red | Red |
| 10 ml | 1.2 N HCl | 8 ml | Red | Red |

The results showed that the aurintricarboxylic acid, ammonium salt solution changed from red to yellow or colorless when reacted with oxidizing chemicals such as hydrogen peroxide and bleach. However, the solution did not change color when exposed to acid or base.

The chemical indicator of the invention has been described with reference to its use as a sterilizing agent in an oxidizing environment. It is to be appreciated that the invention is not limited to use as an indicator for sterilization-type processes, but may be used in other processes employing an oxidizing agent. It is also to be appreciated that the chemical indicator is not specific to one oxidizing agent, such as hydrogen peroxide. Instead, the chemical indicator of the invention can be used for a variety of other oxidizing agents, including ozone, chlorine dioxide, and peracetic acid. It is further to be appreciated that the chemical indicator of the invention is not limited to beneficial uses in the presence of vapor or gaseous oxidizing agents. Instead, the chemical indicator also processes useful properties in the presence of liquid phase or other oxidizing agents.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A chemical indicator comprising:
    an aurin moiety in a substrate to detect the presence of an oxidizing agent after exposure of less than two hours,
    wherein the aurin moiety is a solid, and
    wherein the substrate comprises a gas permeable pouch and the aurin moiety is disposed within the pouch.

2. The chemical indicator of claim 1, wherein the oxidizing agent is hydrogen peroxide.

3. A chemical indicator comprising:
    an aurin moiety in a substrate to detect the presence of an oxidizing agent after exposure of less than two hours,
    wherein the aurin moiety is a solid, and
    wherein the substrate is a tube and the aurin moiety is disposed within a portion of the tube, and the chemical indicator further comprises at least one gas permeable stopper disposed in or on the tube, and the aurin moiety is disposed in the tube adjacent the stopper.

4. The chemical indicator of claim 3, wherein the oxidizing agent is hydrogen peroxide.

* * * * *